(12) United States Patent
Nogami et al.

(10) Patent No.: US 10,585,089 B2
(45) Date of Patent: Mar. 10, 2020

(54) ANALYSIS DEVICE AND ANALYSIS METHOD

(71) Applicant: HITACHI HIGH-TECHNOLOGIES CORPORATION, Tokyo (JP)

(72) Inventors: Makoto Nogami, Tokyo (JP); Shinya Ito, Tokyo (JP); Tadao Yabuhara, Tokyo (JP)

(73) Assignee: HITACHI HIGH-TECHNOLOGIES CORPORATION, Tokyo (JP)

(*) Notice: Subject to any disclaimer, the term of this patent is extended or adjusted under 35 U.S.C. 154(b) by 192 days.

(21) Appl. No.: 15/320,406

(22) PCT Filed: Jun. 17, 2015

(86) PCT No.: PCT/JP2015/067386
§ 371 (c)(1),
(2) Date: Dec. 20, 2016

(87) PCT Pub. No.: WO2016/006398
PCT Pub. Date: Jan. 14, 2016

(65) Prior Publication Data
US 2017/0160273 A1    Jun. 8, 2017

(30) Foreign Application Priority Data

Jul. 7, 2014  (JP) .................................. 2014-139281

(51) Int. Cl.
*G01N 35/02*    (2006.01)
*G01N 33/543*   (2006.01)
(Continued)

(52) U.S. Cl.
CPC ....... *G01N 33/54326* (2013.01); *G01N 15/12* (2013.01); *G01N 15/1209* (2013.01);
(Continued)

(58) Field of Classification Search
None
See application file for complete search history.

(56) References Cited

U.S. PATENT DOCUMENTS

2008/0217254 A1    9/2008  Anderson
2008/0241957 A1   10/2008  Shibata et al.
(Continued)

FOREIGN PATENT DOCUMENTS

CN    101275962 A    10/2008
JP    61-161439 A     7/1986
(Continued)

OTHER PUBLICATIONS

International Search Report, PCT/JP2015/067386, dated Sep. 29, 2015, 2 pgs.
(Continued)

*Primary Examiner* — Erik B Crawford
(74) *Attorney, Agent, or Firm* — Volpe and Koenig, P.C.

(57) ABSTRACT

When using an immunological analysis method wherein antigen-antibody reactions are used to form complexes of microparticles and a substance being measured, purifying, then measuring by spectroscopy, and a mass spectrometry method wherein antigen-antibody reactions are used to form complexes of microparticles and a substance being measured, purifying, then measuring with a mass spectrometer, the amount of the complex flowing in the flow path for immunological analysis and the amount of the complex flowing in the flow path for mass spectrometry are unknown, so the substance being measured cannot be accurately quantified even when merging information obtained from immunological analysis and information obtained from mass spectrometry. The invention provides a mechanism for quan- (Continued)

tifying the complexes after formation of the complexes, on the flow path for mass spectrometry and the flow path for immunological analysis.

7 Claims, 7 Drawing Sheets

(51) Int. Cl.

| | | |
|---|---|---|
| *G01N 15/12* | (2006.01) | |
| *G01N 30/72* | (2006.01) | |
| *G01N 33/82* | (2006.01) | |
| *G01N 35/08* | (2006.01) | |
| *G01N 35/10* | (2006.01) | |
| *G01N 15/00* | (2006.01) | |

(52) U.S. Cl.
CPC ......... *G01N 30/7233* (2013.01); *G01N 33/82* (2013.01); *G01N 35/025* (2013.01); *G01N 35/08* (2013.01); *G01N 35/1095* (2013.01); *G01N 2015/0065* (2013.01)

(56) References Cited

U.S. PATENT DOCUMENTS

| | | |
|---|---|---|
| 2011/0287446 A1 | 11/2011 | Kanda et al. |
| 2013/0324505 A1 | 12/2013 | Thadhani et al. |

FOREIGN PATENT DOCUMENTS

| | | |
|---|---|---|
| JP | 01-187459 A | 7/1989 |
| JP | 07-318559 A | 12/1995 |
| JP | 10-288601 A | 10/1998 |
| JP | 2006-121935 A | 5/2006 |
| JP | 2014-506332 A | 3/2014 |
| WO | 2010/092958 A1 | 8/2010 |

OTHER PUBLICATIONS

Chinese Office Action dated May 25, 2018 for the Chinese Patent Application No. 201580037164.4.

[Fig. 1]
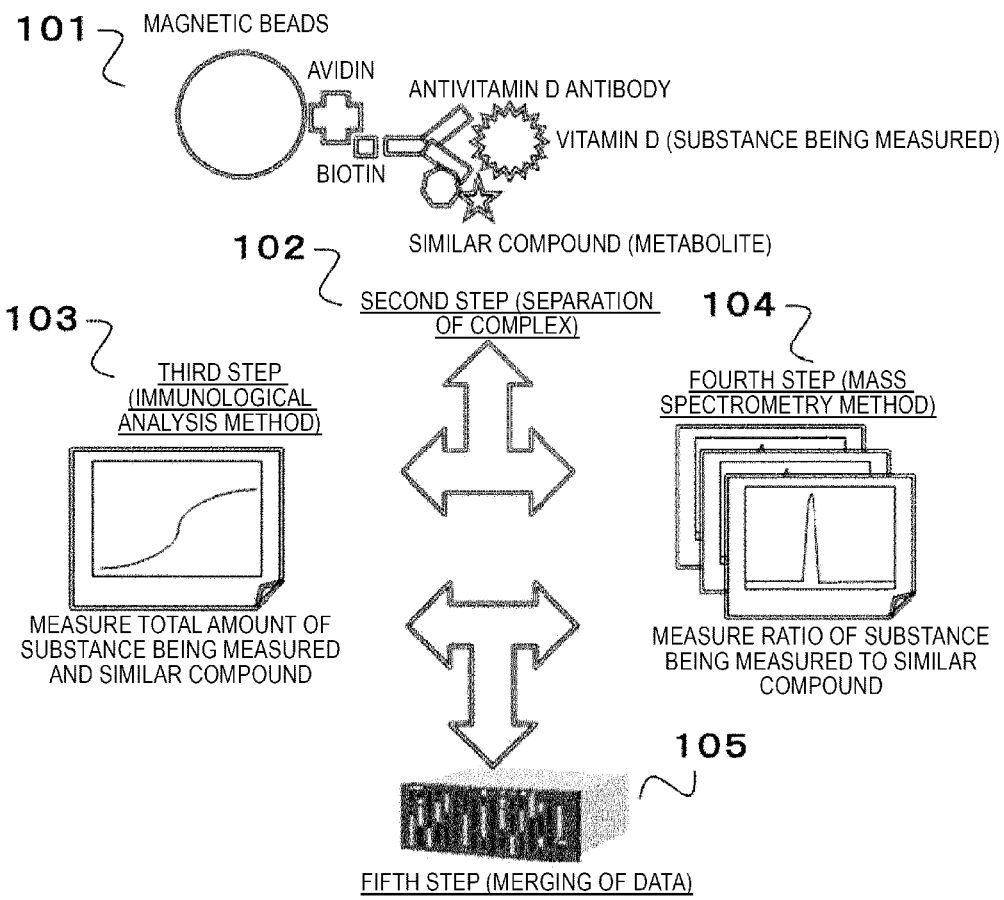

[Fig. 2]
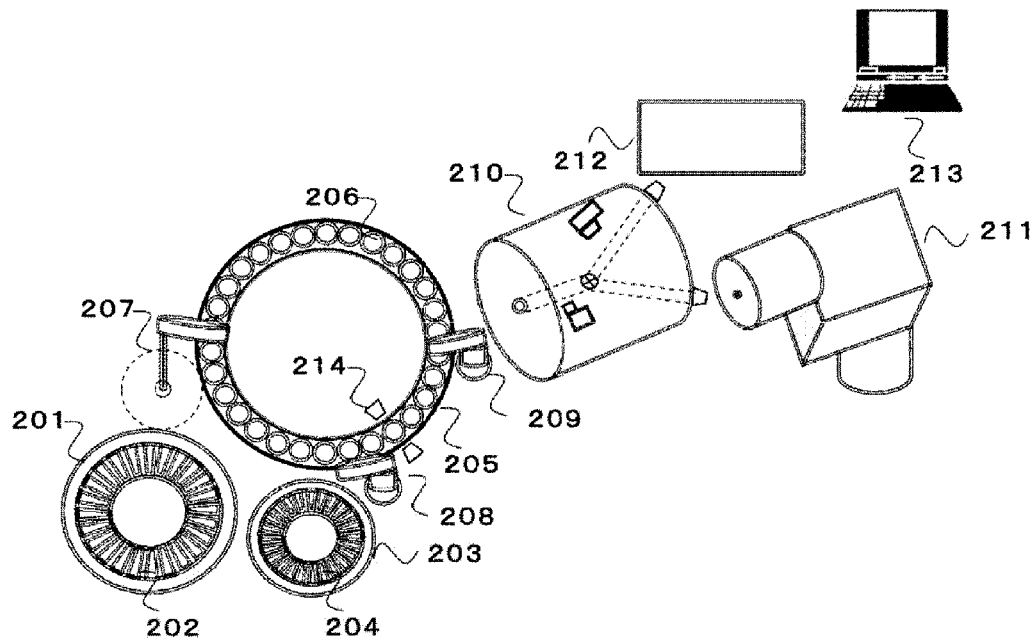
[Fig. 3]
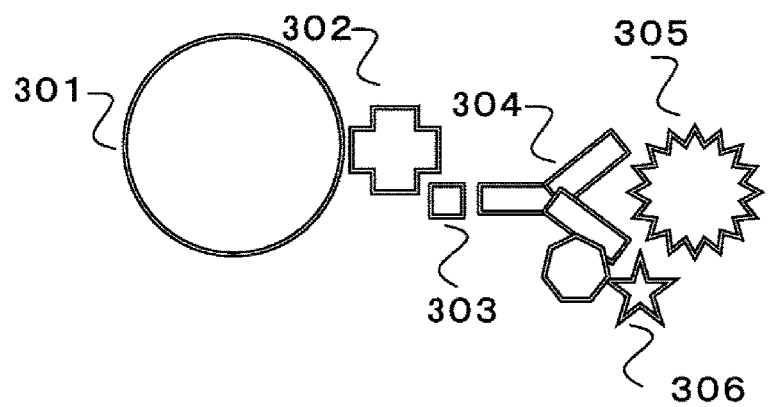

[Fig. 4]
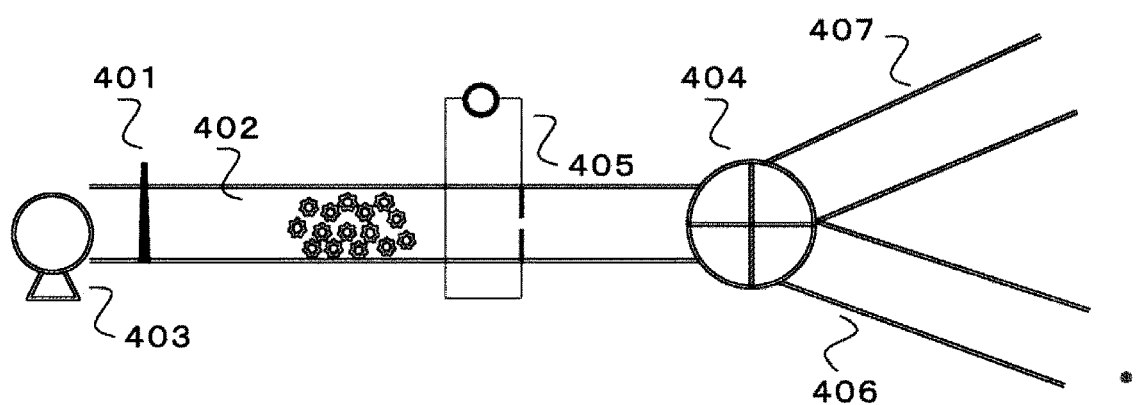
[Fig. 5]
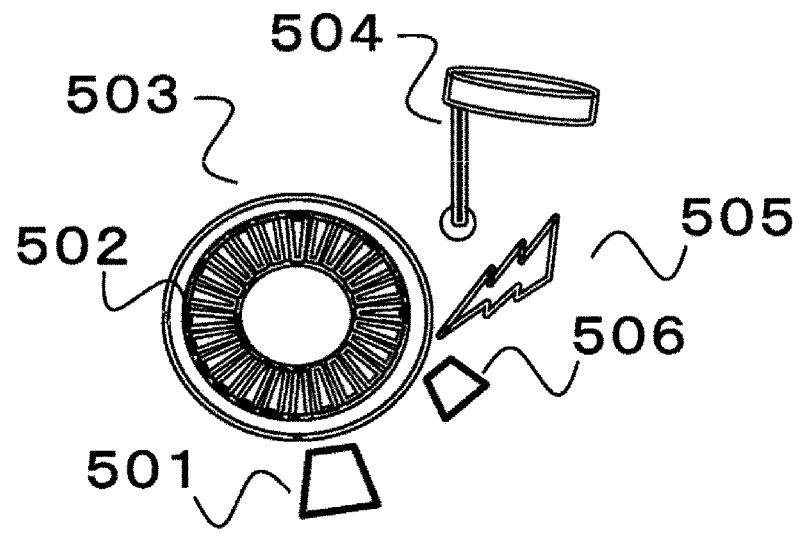

[Fig. 6]
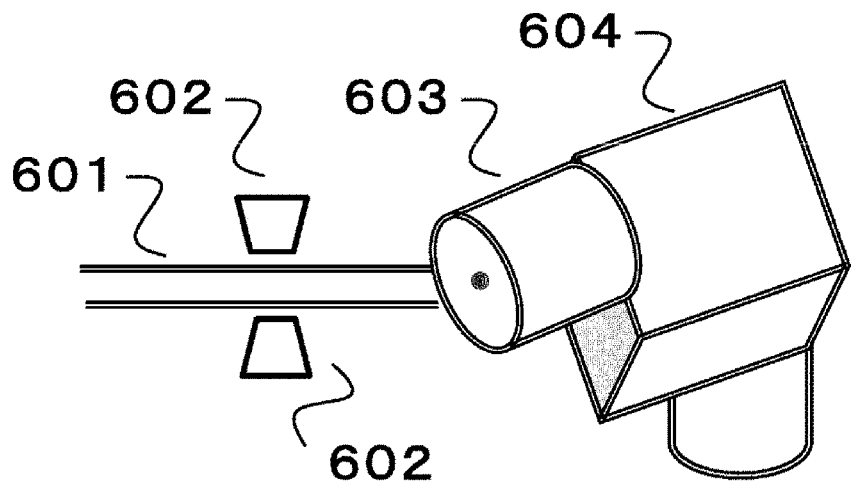
[Fig. 7]
| COMPONENT | PEAK INTENSITY (OR PEAK AREA) | PROPORTION OF PRESENCE AMOUNT AT PEAK INTENSITY (%) | DETAILS WHEN QUANTITATIVE VALUE OBTAINED BY IMMUNOLOGICAL ANALYSIS UNIT IS 30 ng/mL (ng/mL) |
|---|---|---|---|
| 25-OH $D_3$ | 1,404,000 | 54 | 16.2 |
| 25-OH $D_2$ | 1,170,000 | 45 | 13.5 |
| 24,25-(OH)$_2$ $D_3$ | 25,740 | 0.99 | 0.297 |
| VITAMIN $D_2$ | 260 | 0.01 | 0.003 |

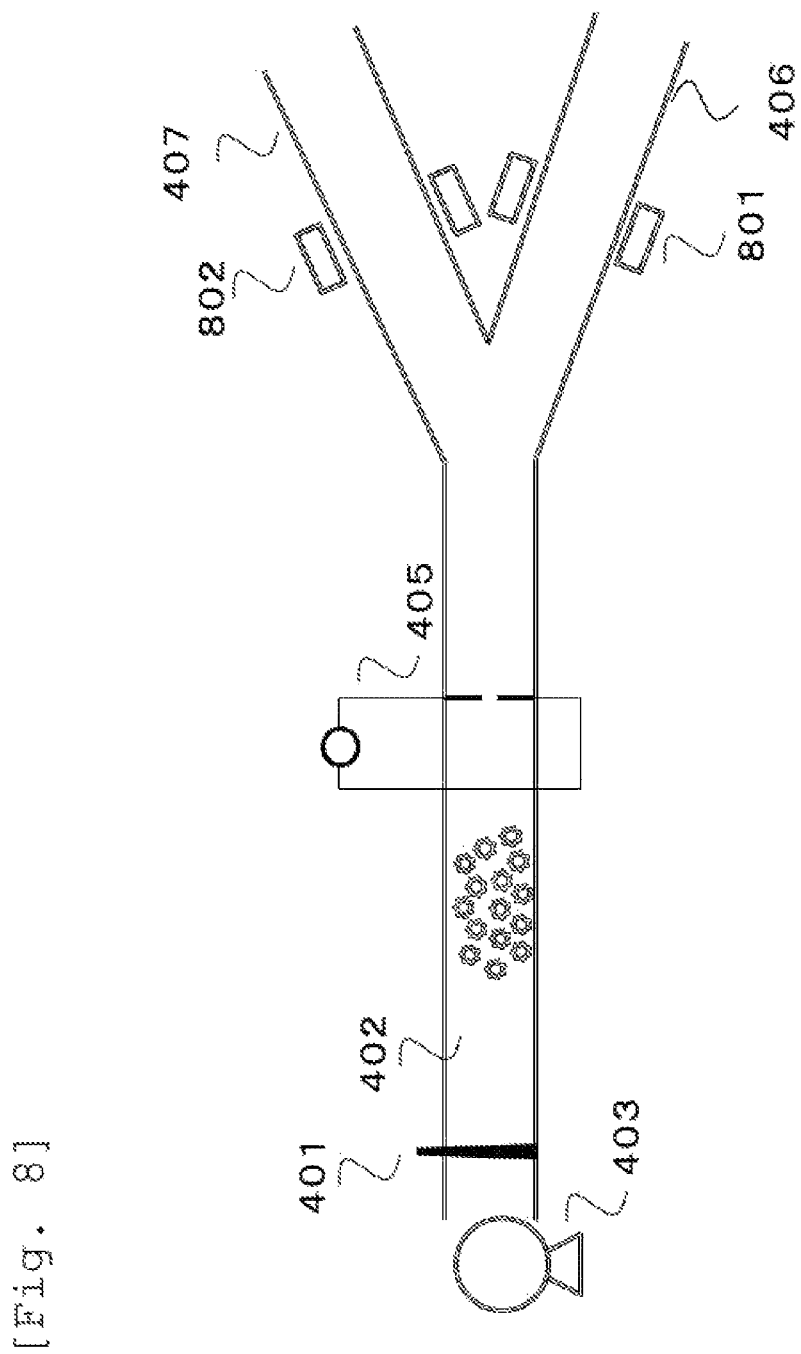
[Fig. 8]

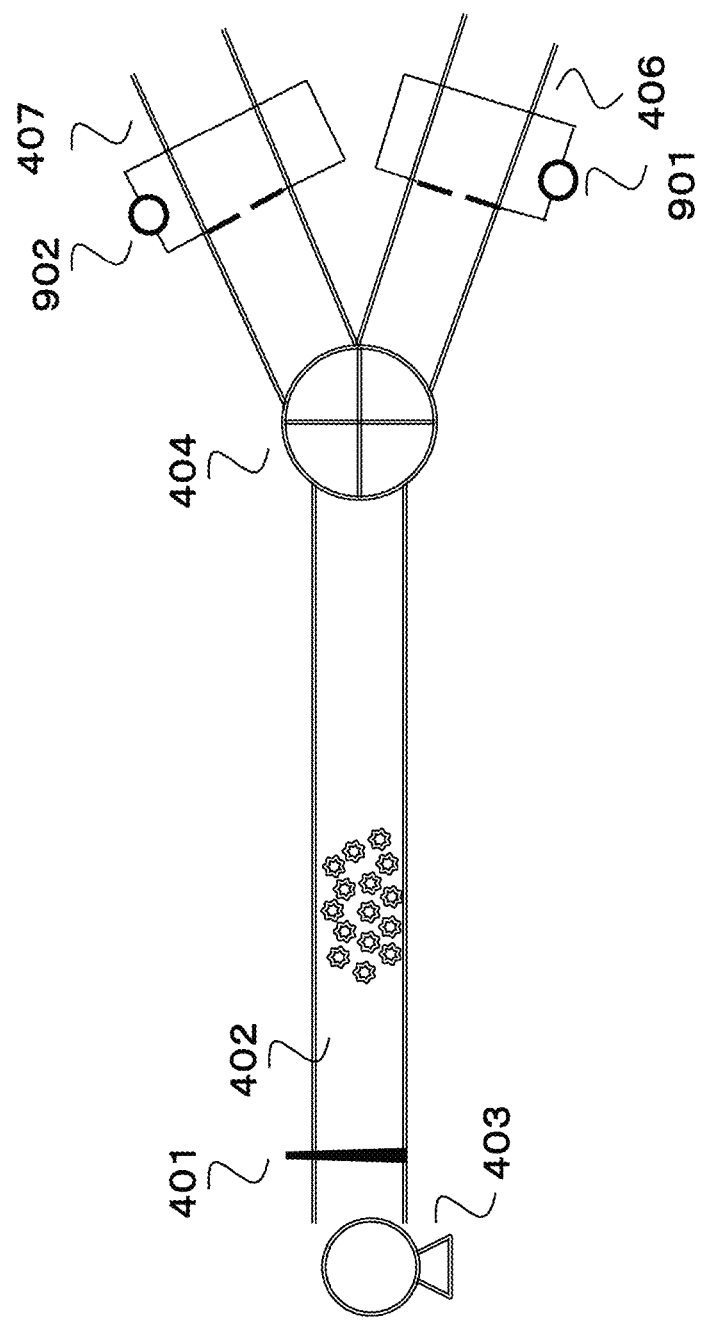
[Fig. 9]

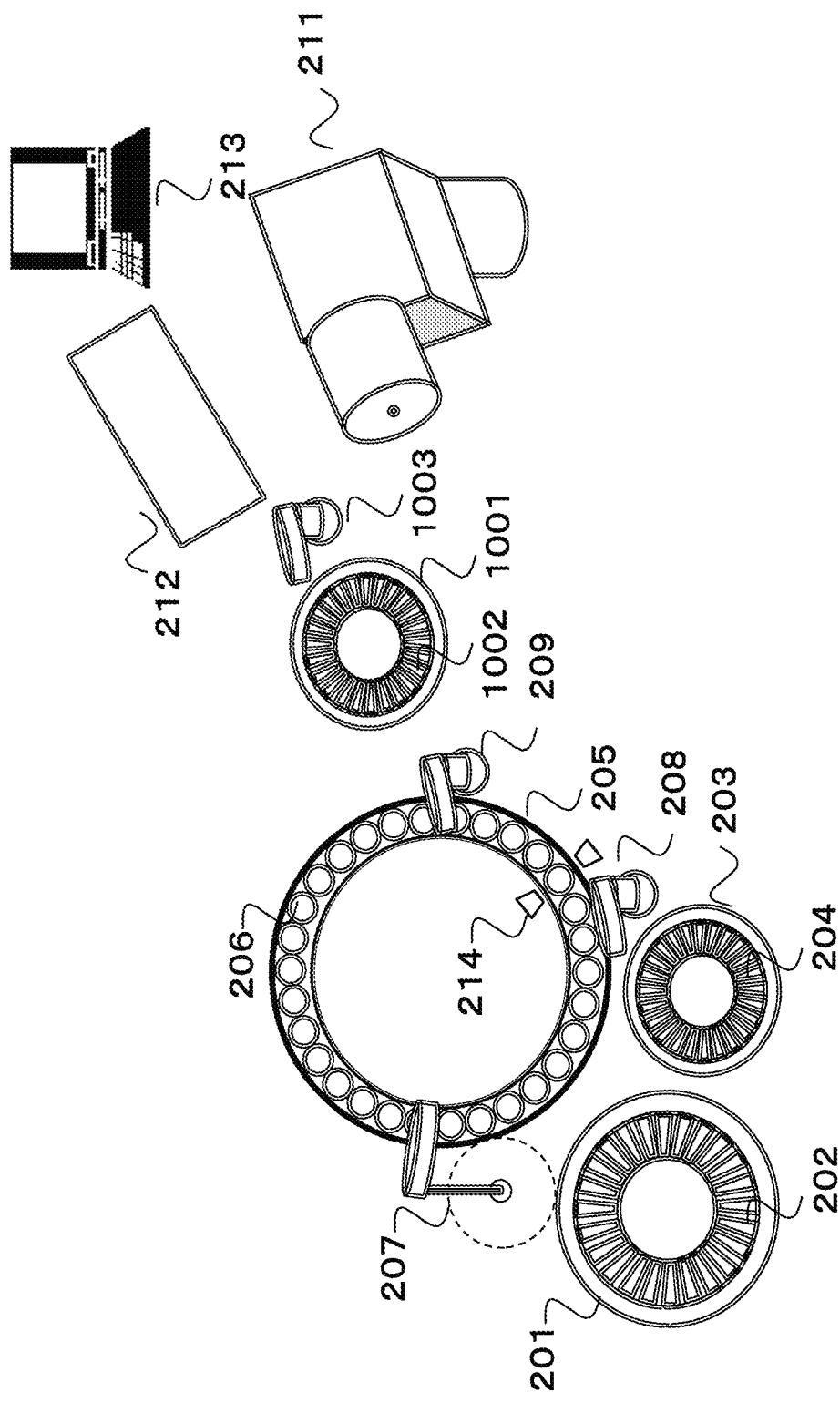
[Fig. 10]

ANALYSIS DEVICE AND ANALYSIS METHOD

TECHNICAL FIELD

The invention relates to an analysis device and an analysis method.

BACKGROUND ART

US2008/0217254 (PTL 1) discloses the background art of the technical field of this invention. The document discloses "an automated device including a rotary microparticles (magnetic beads) trapping unit which is disposed on a capillary flow path, and a high speed liquid chromatograph-tandem mass spectrometer, in which the microparticles trapping unit complements and washes a complex obtained by the bonding of microparticles previously bonded with an antibody and a substance being measured, and elutes the substance being measured from the microparticles, and a method thereof". JP-A-1-187459 also discloses the background art of the technical field of this invention. The document discloses "an immunological analysis method of allowing an antigen-antibody reaction in a reaction solid phase to isolate a complex obtained by the bonding of microparticles previously bonded with an antibody and a substance being measured due to the antigen-antibody reaction from the reaction solid phase, performing measurement using the spectroscopy, and quantifying a target component".

CITATION LIST

Patent Literature

PTL 1: US2008/0217254
PTL 2: JP-A-1-187459

SUMMARY OF INVENTION

Technical Problem

PTL 1 discloses a technology of complementing and cleaning a complex obtained by the bonding of microparticles previously bonded with an antibody and a substance being measured, performing an elution treatment of the substance being measured from the microparticles, and performing measurement with a high speed liquid chromatograph-tandem mass spectrometer (hereinafter, this technology is referred to as a mass spectrometry method). PTL 2 discloses a technology of allowing an antigen-antibody reaction in a reaction solid phase to isolate a complex obtained by the bonding of microparticles previously bonded with an antibody and a substance being measured due to the antigen-antibody reaction from the reaction solid phase, and performing measurement using the spectroscopy (hereinafter, this technology is referred to as an immunological analysis method).

In purifying treatments of these two technologies, a step of forming a complex of microparticles and a substance being measured by using the antigen-antibody reaction is commonly performed. Meanwhile, regarding the information obtained from the measurement, in the immunological analysis method, the measurement is performed regarding the complex obtained by the bonding of microparticles and a substance being measured using the spectroscopy, and accordingly, information regarding the total amount of the substance being measured which is bonded with the complex is obtained. The immunological analysis method is a simple and high-sensitivity measurement technology, and thus it is suitable for quantitative measurement of minor components, but there is a problem regarding cross reactivity. The cross reactivity is a phenomenon in which an antibody also traps, for example, molecules having a similar structure such as metabolites of the substance being measured (similar compounds), in addition to the substance being measured which is to be originally recognized. This phenomenon means that the results of the quantification become higher than true values and the substance being measured cannot be accurately quantified. In the mass spectrometry method, a substance being measured is eluted from a complex obtained by the bonding of microparticles and the substance being measured, the measurement is performed with a mass spectrometer, and information regarding the mass number of the substance being measured and peak intensity of molecules having the mass number are acquired. In the mass spectrometry method, high precious separation of molecules having a similar structure can be performed, and accordingly, the detection of the substance being measured can be performed, even in a case where the cross reaction between the microparticles previously bonded with an antibody and the substance being measured occurs. However, in the mass spectrometry method, it is necessary to ionize a substance being measured. In a case of ionizing a substance being measured in a biological sample, ion suppression due to contaminants in a biological sample occurs. Since this ion suppression significantly affects the accuracy of the quantification, it is necessary to provide an internal standard substance having ionization efficiency equivalent to that of the substance being measured, and a concentration that is previously known. In many cases, a stable isotopic labelling substance of the substance being measured is used as the internal standard substance, but the cost of the stable isotopic labelling substance is extremely high.

An analysis device of the invention obtained by combining the immunological analysis method and the mass spectrometry method with each other has not been reported yet. When the immunological analysis method and the mass spectrometry method are simply combined with each other, a mechanism of forming a complex and then quantifying (separation of known amounts) the complex in a flow path for mass spectrometry and a flow path for immunological analysis is not provided. Accordingly, it is not possible to calculate accurate quantitative values of the substance being measured, in a case of merging information obtained using the mass spectrometry method and information obtained using the immunological analysis method with each other.

Solution to Problem

In order to solve the above-mentioned problems, the analysis device of the invention includes: a sample transportation unit which transports a sample container; a reagent transportation unit which transports a reagent container; a reaction solution transportation unit which transports the reaction container in which reactions are carried out; a sample probe which sucks and discharges a sample from the sample container to the reaction container; a reagent probe which sucks and discharges reagents from the reagent container to the reaction container; a reaction solution probe which sucks and discharges a complex reacted in the reaction container to a separation unit; the separation unit which quantitative-separates the complex for immunological analysis and for mass spectrometry; a mass spectrometry unit which performs measurement of the complex separated for mass spectrometry using a mass spectrometer; an immunological analysis unit which performs measurement of the complex separated for immunological analysis using an optical method; and a control unit which performs data processing.

Advantageous Effects of Invention

The invention provides the analysis device which solves the problem regarding cross reactivity of the immunological analysis method and does not use an internal standard substance having a high cost in the mass spectrometry method.

BRIEF DESCRIPTION OF DRAWINGS

FIG. 1 is a schematic configuration diagram showing an outline of steps of the invention.
FIG. 2 is a schematic view showing a schematic configuration according to one embodiment of an analysis device of the invention.
FIG. 3 is a view explaining a first step according to one embodiment of the analysis device of the invention.
FIG. 4 is a view explaining a second step according to one embodiment of the analysis device of the invention.
FIG. 5 is a view explaining a third step according to one embodiment of the analysis device of the invention.
FIG. 6 is a view explaining a fourth step according to one embodiment of the analysis device of the invention.
FIG. 7 is a view explaining a fifth step according to one embodiment of the analysis device of the invention.
FIG. 8 is a view explaining a second step according to one embodiment of the analysis device disclosed in Example 2 of the invention.
FIG. 9 is a view explaining a second step according to one embodiment of the analysis device disclosed in Example 3 of the invention.
FIG. 10 is a schematic view showing a schematic configuration according to one embodiment of the analysis device disclosed in Example 4 of the invention.

DESCRIPTION OF EMBODIMENTS

Hereinafter, the embodiments of the invention will be described in detail with reference to the drawings. In all drawings for explaining the embodiments, the same reference numerals are generally used for elements having the same mechanism and the repeated descriptions are omitted, if possible.

EXAMPLE 1

As a typical example of the invention, a case of using a vitamin D metabolite as a substance being measured will be described with reference to FIGS. 1 to 7.
[Description of Vitamin D]
Vitamin D is fat-soluble vitamin discovered as an antirachitic factor and has an important role in maintaining homeostasis of a calcium concentration in human blood. Vitamin $D_3$ is produced in a human body. Vitamin $D_2$ is produced in plants or by biosynthesis and is taken into the body as foods or supplements. Vitamin $D_3$ metabolites will be described. Vitamin $D_3$ biosynthetically produced in the skin from 7-dehydrocholesterol is metabolized by 25-hydroxyvitamin $D_3$ (25-OH $D_3$) in the liver, is bonded with vitamin D-binding protein (DBP), and circulates in the body. When a concentration of calcium in the blood becomes equal to or smaller than a normal value, 25-OH $D_3$ is metabolized by 1α,25-dihydroxyvitamin $D_3$ [1α,25-(OH)$_2$ $D_3$] in the kidney. When the concentration of calcium in the blood is recovered, 1α-hydroxylation is prevented and 25-OH $D_3$ is mainly metabolized by 24R,25-dihydroxyvitamin D [24,25-(OH)$_2$ $D_3$]. Vitamin $D_2$ is also metabolized in the same process as in the case of vitamin $D_3$. That is, main vitamin D metabolites in the blood are at least 8 kinds such as vitamin $D_3$, 25-OH $D_3$, 1α,25-(OH)$_2$ $D_3$, 24,25-(OH)$_2$ $D_3$, vitamin $D_2$, 25-OH $D_2$, 1α,25-(OH)$_2$ $D_2$, and 24,25-(OH)$_2$ $D_2$. In a clinical situation, the total amount of 25-OH $D_3$ and 25-OH $D_2$ which are stably present in the blood with a high concentration is used as an index reflecting the concentration of vitamin D in the blood.
[Description of Immunological Analysis Method of Related Art]
In a vitamin D measurement method using the immunological analysis method of the related art, the total amount of 25-OH $D_3$ and 25-OH $D_2$ circulating in the blood is measured and is used as an index reflecting the concentration of vitamin D in the blood. A treatment process of the immunological analysis method is as follows. Since 25-OH $D_3$ and 25-OH $D_2$ which are substances being measured in a biological sample are bonded with DBP, isolation is performed by adding acid, alkali, or a reducing agent. Then, an antibody specifically recognizing substances being measured is previously bonded with the magnetic beads using avidin-biotin bonding to allow a reaction of the treated biological sample. A complex obtained by the bonding of the magnetic beads bonded with an antibody and substances being measured is magnetically collected using a magnet, and washed, and sandwich assay is performed using an enzyme-labelled anti-immunoglobulin antibody. Then, a substrate of an enzyme (luminescent or color reagent) is added and a product of the enzyme reaction is detected using a detector. However, in addition to substances being measured, similar compounds are also trapped depending on the kinds of antibodies used in the immunological analysis method, and accordingly, results of the quantification may become higher than true values. The definition of the "biological sample" here is a biological sample derived from a biological supply source such as a serum, plasma, whole blood, urine, saliva, bile, tear, and cell tissues.
[Description of Mass Spectrometry Method of Related Art]
In a vitamin D measurement method using the mass spectrometry method of the related art, each concentration of 25-OH $D_3$ and 25-OH $D_2$ circulating in the blood is quantified. The quantification is performed by performing relative quantification by previously adding a stable isotopic substance having a known concentration. A treatment process of the mass spectrometry method is as follows. The known amounts of a stable isotopic labelling substance (for example, 25-OH $D_3$-d6) of 25-OH $D_3$ and a stable isotopic labelling substance (for example, 25-OH $D_2$-d6) of 25-OH $D_2$ which are internal standard substances are added to the biological sample. Since 25-OH $D_3$ and 25-OH $D_2$ which are substances being measured in the biological sample are bonded with DBP, the isolation is performed by adding acid, alkali, or a reducing agent. Then, an antibody specifically recognizing substances being measured is previously bonded with the magnetic beads using avidin-biotin bonding to allow a reaction of the treated biological sample. A complex obtained by the bonding of the magnetic beads bonded with an antibody and substances being measured is magnetically collected using a magnet, and washed, acid, alkali, or an organic solvent is added thereto, and the measurement regarding the substances being measured and the internal standard substance isolated from the antibody is performed using a mass spectrometer. In the quantification of 25-OH $D_3$, a ratio of 25-OH $D_3$ to 25-OH $D_3$-d6 is calculated, a sample for a calibration curve including 25-OH $D_3$ having a known concentration is measured, and the concentration of 25-OH $D_3$ is calculated by using a created calibration curve. The concentration of 25-OH $D_2$ is also calculated in the same manner.

[Description of Case of Combination]

As shown in FIG. 1, this example is configured with a first step 101 of forming and purifying a complex of microparticles and a substance being measured using an antigen-antibody reaction, a second step 102 of quantitatively separating the complex purified in the first step, a third step 103 of acquiring information of the total amount of the separated complex by using an immunological analysis method, a fourth step 104 of eluting the substance being measured and similar compounds from the separated complex and acquiring information of a ratio of the substance being measured to the similar compounds by using a mass spectrometry method, and a fifth step 105 of performing accurate quantification of the substance being measured by using the total amount of the complex acquired in the third step and proportions of presence amounts of the substance being measured and the similar compounds acquired in the fourth step.

The definition of the "antigen-antibody reaction" here is a method of separating a component to be measured and impurities by using a bonding reaction between an antigen (component to be measured) and an antibody.

[Description of Analysis Device]

The configuration of the device of this example will be described with reference to FIGS. 2 and 3. The device is configured with a sample transportation unit 201 which transports a sample container 202, a reagent transportation unit 203 which transports a reagent container 204, a reaction solution transportation unit 205 which transports a reaction container 206 in which various reactions are carried out, a sample probe 207 which sucks and discharges a sample from the sample container 202 to the reaction container 206, a reagent probe 208 which sucks and discharges various reagents from the reagent container 204 to the reaction container 206, a reaction solution probe 209 which sucks and discharges a complex reacted in the reaction container 206 to a separation unit 210, the separation unit 210 which quantitative-separates the complex for immunological analysis and for mass spectrometry, a mass spectrometry unit 211 which performs measurement of the complex separated for mass spectrometry using a mass spectrometer, an immunological analysis unit 212 which performs measurement of the complex separated for immunological analysis using an optical method, and a control unit 213 which performs automatic overall control and data processing of various units configuring this device. The sample transportation unit 201, the reagent transportation unit 203, and the reaction container transportation unit 205 will be described using a disc type which performs transportation on an endless track as a transportation mechanism, as an example, but there is no limitation, and a transportation mechanism of transporting on a X-Y axis or a belt conveyer type transportation mechanism may be used. Although not shown, a stirring unit which performs stirring at the time of performing various reactions in a reaction container and a washing unit which washes various probes are installed in the device.

Biological samples, in this example, a serum or plasma which is a specimen, a calibrator sample, and a quality control (QC) sample are accommodated in the sample container 202. Sodium hydroxide having a concentration of 1 mol/L which is a reagent for isolating a vitamin D metabolite as a substance being measured from DBP, the magnetic beads subjected to antibody binding, and phosphate buffered saline (pH 7.4) having a concentration of 10 mmol/L which is a washing solution are accommodated in the reagent container 204. The magnetic beads subjected to antibody binding are previously configured by performing avidin-biotin bonding of an antivitamin D antibody 304 with a magnetic beads 301 using avidin 302 and biotin 303. In this example, the magnetic beads subjected to antibody binding which are obtained by bonding 10 µg of anti 25-OH $D_3$ antibody manufactured by ImmunDiagnostik with the magnetic beads (approximately, 1 mg) having a diameter of 300 nm suspended in 50 µL of phosphate buffered saline having a concentration of 10 mmol/L (pH 7.4) in a slurry form using an avidin-biotin reaction, were used. In addition to sodium hydroxide as in this example, as the reagents for the isolation from DBP, formic acid or trifluoroacetic acid can be used as acid, dithiothreitol or mercaptoethanol can be used as a reducing agent, and urea, Tween20, TritonX-100, or sodium dodecyl sulfate can be used as a modifying agent. Regarding surface modification of the magnetic beads, in addition to the magnetic beads subjected to surface modification using avidin for an avidin-biotin reaction as in this example, the magnetic beads subjected to surface modification with a hydroxysuccinimide group, 1,1-carbonyldiimidazole group, protein A, protein G, and anti-mouse antibody can also be used. As the washing solution, a tris-hydrochloric acid buffer solution, a HEPES buffer solution, or water can also be used, in addition to phosphate buffered saline as in this example.

[Description of First Step]

A flow of the measurement of this example will be described. The first step 101 will be described. In the first step 101, a complex of magnetic beads and a substance being measured is formed using an antigen-antibody reaction and purified. The sample transportation unit 201 and the reaction container transportation unit 205 rotate to a predetermined position below the sample probe 207. 100 µL of the serum (or a calibrator sample or a QC sample) is sucked and discharged from a sample container to the reaction container 206 by using the sample probe 207. Then, the reagent transportation unit 203 and the reaction container transportation unit 205 rotate to a predetermined position below the reagent probe 208. 20 µL of sodium hydroxide having a concentration of 1 mol/L is sucked and discharged from the reagent container 204 to the reaction container 206 accommodating the serum by using the reagent probe 208. Then, the magnetic beads (approximately, 1 mg) subjected to antibody binding suspended in 50 µL of phosphate buffered saline having a concentration of 10 mmol/L (pH 7.4) in a slurry form are sucked and discharged from the reagent container 204 to the reaction container 206 in which sodium hydroxide is added to the serum by using the reagent probe 208. The substance being measured in the biological sample and the magnetic beads subjected to antibody binding are reacted in the reaction container 206 at room temperature for 10 minutes and a complex obtained by bonding the substance being measured and the magnetic beads subjected to antibody binding with each other is formed. Then, the reaction container transportation unit 205 rotates to a predetermined position below a magnet 214, the complex in the reaction container 206 is magnetically collected, the reaction solution is sucked from the reaction container 206 and discharged as a waste solution by using the reagent probe 208. The reagent transportation unit 203 and the reaction container transportation unit 205 rotate to a predetermined position below the reagent probe 208. 200 µL of phosphate buffered saline (pH 7.4) having a concentration of 10 mmol/L is sucked and discharged from the reagent container 204 by using the reagent probe 208, the washing of the complex is performed, and nonspecific reaction is reduced. This magnetically collecting-washing operation is performed three times. Then, the reaction solution transportation unit 205 rotates to a predetermined position below the reaction solution probe 209. The total amount of the complex suspended in phosphate buffered saline having a concentration of 10 mmol/L (pH 7.4) in the reaction container 206 in a slurry form is sucked and discharged to the separation unit 210 by using the reaction solution probe 209.

[Description of Second Step]

The second step 102 will be described. In the second step 102, the complex purified in the first step is quantitatively separated. The separation unit 210 will be described with reference to FIG. 4. The separation unit 210 is configured with an injector 401 which introduces the complex discharged from the reaction solution probe 209 to the separation unit 210, a flow path 402, a pump 403 which is positioned in a front stage of the injector 401 and sends a solvent to the flow path 402, an active flow splitter 404 which is positioned in a rear stage of the flow path 402 and positioned on the branched portion of the flow path 402, a particle distribution measurement device (for example, Coulter counter or the like) 405 which measures the amount of the complex on the flow path 402 between the injector 401 and the active flow splitter 404 in real time, a flow path for mass spectrometry 406 which is positioned in the rear stage of the active flow splitter 404 and sends the complex to the mass spectrometry unit 211, and a flow path for immunological analysis 407 which is positioned in the rear stage of the active flow splitter 404 and sends the complex to the immunological analysis unit 212. An electrolytic solution, that is, in this example, phosphate buffered saline (pH 7.4) having a concentration of 10 mmol/L is sent into the flow path 402, and the particle distribution measurement device 405 used for measurement of the amount of the complex measures a change in electric resistance when the complex passes a pore in the particle distribution measurement device 405 to detect the amount of the complex. The separation unit 210 has a mechanism of calculating the amount of the complex sent to the flow path for mass spectrometry 406 and the flow path for immunological analysis 407 based on a measurement value obtained from the particle distribution measurement device 405, a distance from the particle distribution measurement device 405 to the active flow splitter 404, an inner diameter of the flow path 402, a flow rate of an electrolytic solution flowing through the flow path 402, and a switch time of the active flow splitter 404.

In this example, the distance from the particle distribution measurement device 405 to the active flow splitter 404 was set as 30 cm, the inner diameter of the flow path 402 was set as 0.2 mm, a rate of the electrolytic solution flowing through the flow path 402 was set as 0.1 mL/min, the active flow splitter 404 was opened for 6 seconds in a direction of the flow path for immunological analysis 407 to set to be switched to the flow path for mass spectrometry 406 after the complex is sent, and the equivalent amounts of the complex are separated into the flow path for mass spectrometry 406 and the flow path for immunological analysis 407. The amount of the complex arriving the flow path for mass spectrometry 406 and the flow path for immunological analysis 407 is adjusted by changing the switch time of the active flow splitter 404.

[Description of Third Step]

The third step 103 will be described. In the third step 103, the information regarding the total amount of the separated complex is obtained using the immunological analysis method. The immunological analysis unit 212 will be described with reference to FIG. 5. The immunological analysis unit 212 is configured with a magnet 501, a reagent container for immunological analysis 502 which holds the complex sent from the flow path for immunological analysis 407 and a reagent for immunological analysis, a reagent transportation unit for immunological analysis 503 which transports a reagent container for immunological analysis 502, a probe for immunological analysis 504 which sucks and discharges the reagent for immunological analysis from the reagent container for immunological analysis 502 holding the reagent for immunological analysis to the reagent container for immunological analysis 502 holding the complex, a light source 505 which irradiates the complex in a reaction chamber 505 with light, and a photometer 506. As the reagent for immunological analysis, antigloblulin which is a secondary antibody which is selectively bonded with a primary antibody is used. This secondary antibody is subjected to fluorescent labeling and can be quantified using the spectroscopy.

A flow of the measurement of immunological analysis unit 212 will be described. The complex sent from the flow path for immunological analysis 407 is held in the hollow reagent container for immunological analysis 502. The reagent transportation unit for immunological analysis 503 rotates to a predetermined position below the probe for immunological analysis 504. The secondary antibody subjected to labeling dissolved in 50 µL of phosphate buffered saline (pH 7.4) having a concentration of 10 mmol/L is sucked and discharged from a sample container to the reagent container for immunological analysis 502 holding the complex by using the probe for immunological analysis 504. The reagent transportation unit for immunological analysis 503 rotates to a predetermined position below the magnet 501, the complex-secondary antibody is magnetically collected, and the complex-secondary antibody is washed. Next, the reagent transportation unit for immunological analysis 503 rotates to a predetermined position below the light source 505, light is emitted from the light source 505, and measured using the photometer 506. In the third step, the data of the total amount of the complex separated in the second step 102 is calculated using the immunological analysis method. The appended document discloses that the cross reaction of the anti 25-OH $D_3$ antibody manufactured by ImmunDiagnostik in this example is performed with 100% of 25-OH $D_3$, 68% of 25-OH $D_2$, 100% of 24,25-$(OH)_2$ $D_3$, and 0.3% of vitamin $D_2$. That is, in a case of performing the immunological analysis method using the complex obtained by bonding microparticles bonded to the antibody, and the substance being measured, the bonding of 24,25-$(OH)_2$ $D_3$ and vitamin $D_2$ other than the total amount of 25-OH $D_3$ and 25-OH $D_2$ which are substances being measured is also performed, and the quantitative values of the total amount of 25-OH $D_3$, 25-OH $D_2$, 24,25-$(OH)_2$ $D_3$, and vitamin $D_2$ forming the complex are calculated.

[Description of Fourth Step]

The fourth step 104 will be described. In the fourth step 104, the substance being measured and similar compounds are eluted from the separated complex, and information of a ratio of the substance being measured to the similar compounds is obtained by using the mass spectrometry method. The mass spectrometry unit 211 will be described with reference to FIG. 6. The mass spectrometry unit 211 is configured with a flow path 601 linked to the flow path for mass spectrometry 406, a magnet 602 which is disposed on the outer side of a tube of the flow path 601 and magnetically collects the complex, a ion source 603 which applies high pressure and a high voltage to the substance being measured for ionizing, and a mass spectrometer 604. The complex sent to the flow path 601 is magnetically collected by the magnet 602 disposed on the outer side of the tube of the flow path 601, a solvent in the flow path 601 is changed to 0.1% glycine hydrochlorate which is an elution solution to isolate the substances being measured bonded with the antibody on the complex and similar compounds, and the substances are introduced to the ion source 603. After performing ionizing by the ion source 603, the mass number is measured by the mass spectrometer 604. In addition to glycine hydrochlorate as in this example, as the elution solvent, an acid aqueous solution such as formic acid, a basic aqueous solution such as sodium hydroxide, and an organic solvent such as methanol can also be used. As the ionization method using the ion source 603, Atomospheric Pressure Chemical Ionization (APCI) was used in this example. As other ionization methods, Electrospray Ionization (ESI) can also be used. In this example, the mass spectrometer 604 performs analysis of a component to be measured in a Selected Reaction Monitoring (SRM) mode by using a triple-quadrupole mass spectrometer. As the mass spectrometer 604, a Quadrupole Mass Spectrometer or an ion trap type mass spectrometer can also be used. Data items regarding a peak intensity or a peak area based on transition of 25-OH $D_2$, 25-OH $D_3$, 24,25-$(OH)_2$ $D_3$, and vitamin $D_2$ which are substances being measured isolated from the complex separated in the second step 102 are calculated. In this example, MS/MS analysis was performed in the Selected Reaction Monitoring (SRM) mode by using the triple-quadrupole mass spectrometer, the transition of each substance being measured was set so that the transition of 25-OH $D_3$ was set as Q1/Q3=401.3/383.3, the transition of 25-OH $D_2$ was set as Q1/Q3=413.3/395.3, the transition of 24,25-$(OH)_2$ $D_3$ was set as 417.3/399.3, and the transition of vitamin $D_2$ was set as 397.3/379.3, and data of peak intensity was obtained. Each peak intensity or peak area indicates proportions of presence amounts of 25-OH $D_2$, 25-OH $D_3$, 24,25-$(OH)_2$ $D_3$, and vitamin $D_2$ bonded to the complex.

The purification of liquid-liquid extraction or solid phase extraction of the substance being measured and similar compounds isolated from the antibody or treatment of derivatization may be performed. The definition of the "solid phase extraction" here is a method of separating a component to be measured and impurities by using a phenomenon that solutes contained in a solution or a suspension (moving phase) are adsorbed to a solid (solid phase) depending on affinity while flowing through the solid or solutes flow through the solid as they are. The definition of the "liquid-liquid extraction" is a method of separating a component to be measured and impurities by using a difference of solubility between solutes contained in a solution or a suspension (moving phase) and other solvents (mainly water and non-polar organic solvent). As the derivatization, a method of performing derivatization by adding a Cookson-type reagent, for example, a derivatizing reagent of 4-phenyl-1,2,4-triazoline-3,5-dione (PTAD) to the substance being measured and internal standard substance isolated from the antibody to improve ionization efficiency is also used. In this case, the transition of each substance being measured is set so that the transition of a 25-OH $D_3$-PTAD derivative is set as Q1/Q3=576.3/298.3, the transition of a 25-OH $D_2$-PTAD derivative is set as Q1/Q3=588.3/298.3, the transition of a 24,25-$(OH)_2$ $D_3$-PTAD derivative is set as 592.3/298.3, and a vitamin $D_2$-PTAD derivative is set as 572.3/298.3. The definition of the "derivatization" here is modification performed at a degree not significantly changing the structures or properties, such as introduction of functional groups in the substance being measured, oxidization, reducing, or substitution of atoms. The derivatization is used for preventing ion suppression due to contaminants by improving ionization efficiency and changing the mass number of the substance being measured to a high mass range, in a case where the sensitivity of MS is insufficient. In addition to PTAD, examples of the derivatizing reagent include 1,2,4-triazoline-3,5-dione (TAD), 4-amino-1,2,4-triazoline-3,5-dione (ATAD), 4-pentafluorobenzyl-1,2,4-triazoline-3,5-dione (PFBTAD), 4-[4-(6-methoxy-2-benzoxazolyl) phenyl-1,2,4-triazoline-3,5-dione (MBOTAD), and 4-[2-(6,7-dimethoxy-4-methyl-3-oxo-3,4-dihydroquinoxalinyl) ethyl-3,5-dione (DMEQTAD).

[Description of Fifth Step]

The fifth step 105 will be described with reference to FIG. 7. In the fifth step 105, the accurate quantification of the substance being measured is performed using data regarding the total amount of the complex obtained in the third step and data regarding the proportions of presence amounts of the substance being measured and the similar compound obtained in the fourth step. A quantitative value obtained using the immunological analysis method in the third step 103 was 30 ng/mL. Meanwhile, a peak area value of 25-OH $D_3$ obtained using the mass spectrometry method in the fourth step 104 was 1,404,000, a peak area value of 25-OH $D_2$ was 1,170,000, a peak area value of 24,25-$(OH)_2$ $D_3$ was 25,740, and a peak area value of vitamin $D_2$ was 260. A proportion of the presence amount of 25-OH $D_3$ with the peak intensity is 54%, a proportion of the presence amount of 25-OH $D_2$ is 45%, a proportion of the presence amount of 24,25-$(OH)_2$ $D_3$ is 0.99%, and a proportion of the presence amount of vitamin $D_2$ is 0.01%. In the second step 102, the equivalent amounts of the complex are set to be separated into the flow path for mass spectrometry 406 and the flow path for immunological analysis 407 and the amounts of the complex introduced to the mass spectrometry unit 211 and the immunological analysis unit 212 are equivalent to each other. That is, when accurate quantitative values of 25-OH $D_2$, 25-OH $D_3$, 24,25-$(OH)_2$ $D_3$, and vitamin $D_2$ are calculated using quantitative values obtained in the third step 103 and the proportions of the presence at the peak intensity obtained in the fourth step 104, a quantitative values of 25-OH $D_3$ is 16.2 ng/mL, a quantitative values of 25-OH $D_2$ is 13.5 ng/mL, a quantitative values of 24,25-$(OH)_2$ $D_3$ is 0.297 ng/mL, a quantitative values of vitamin $D_2$ is 0.003 ng/mL. The quantitative value of 30 ng/mL obtained using the immunological analysis method in the third step 103 indicates the total amount of 25-OH $D_2$, 25-OH $D_3$, 24,25-$(OH)_2$ $D_3$, and vitamin $D_2$, but it is possible to obtain an accurate quantitative value by calculating quantitative values of the substance being measured using the data regarding the total amount of the complex obtained in the third step and data regarding the proportions of presence amounts of the substance being measured and the similar compound obtained in the fourth step, in the fifth step 105.

The invention is not limited to the examples described above and includes various modification examples. For example, the examples described above have been described in detail for describing the invention for easy understanding and the invention is not limited to including all configurations described above. A part of a configuration of a certain example can be replaced with a configuration of another example and a configuration of an example can be added to a configuration of a certain example. In addition, addition, deletion, and replacement of other configurations can be performed for a part of the configuration of each example.

Some or all of the configurations, functions, processing units, and processing procedures described above may be realized with hardware by installing an integrated circuit, for example. The configurations and functions described above may be realized with software by interpreting and executing programs realizing the functions by a processor. Information such as programs, tables, and files realizing the respective functions can be stored in a storage device such as a memory, a hard disk, or a Solid State Drive (SSD), or a storage medium such as an IC card, an SD card, or a DVD.

Control lines or information lines indicate lines considered to be necessary for the description and do not necessarily indicate all of control lines or information lines in the product. In practice, all constituent elements may be connected to each other.

Hereinafter, as described in this example, in the invention, it is possible to provide an analysis device which solves the cross reactivity of the immunological analysis method and does not use an internal standard substance having a high cost in the mass spectrometry method, by calculating quantitative values based on the quantitative value obtained using the immunological analysis method in the third step 103 and the proportions of peak intensity of the substance being measured and the similar compounds obtained using the mass spectrometry method in the fourth step 104.

EXAMPLE 2

Next, an analysis device of Example 2 of the invention will be described with reference to FIG. 8. FIG. 8 is a view explaining a second step according to one embodiment of the analysis device disclosed in Example 2 of the invention. The configuration of the analysis device of this example which is different from that in Example 1 will be described. This example is different therefrom in that an electromagnet is used for switching of the flow path for mass spectrometry 406 and the flow path for immunological analysis 407 in the separation unit 210 in the second step 102. In this example, only the second step 102 is different from that in Example 1 and other configurations are the same. The configuration of the analysis device of this example will be described.

The separation unit 210 of this example is configured with the injector 401 which introduces the complex discharged from the reaction solution probe 209 to the separation unit 210, the flow path 402, the pump 403 which is positioned in a front stage of the injector 401 and sends a solvent to the flow path 402, the particle distribution measurement device 405 which is provided in a front stage of a portion which is branched into two and provided in the rear stage of the injector 401 and the rear stage of the flow path 402, the flow path for mass spectrometry 406 which is a flow path on one side which is branched into two and provided in the rear stage of the flow path 402 and sends the complex to the mass spectrometry unit 211, the flow path for immunological analysis 407 which is a flow path on the other side and sends the complex to the immunological analysis unit 212, an electromagnet 801 which is disposed on the outer side of the tube of the flow path for mass spectrometry 406, and an electromagnet 802 which is disposed on the outer side of the tube of the flow path for immunological analysis 407. Magnetic forces of the electromagnet 801 and the electromagnet 802 are controlled by turning on and off the currents flowing through the electromagnet 801 and the electromagnet 802 to control the amounts of the complex flowing through the flow path for mass spectrometry 406 and the flow path for immunological analysis 407.

The separation unit 210 has a mechanism of calculating the amount of the complex sent to the flow path for mass spectrometry 406 and the flow path for immunological analysis 407 based on a measurement value obtained from the particle distribution measurement device 405, a distance from the particle distribution measurement device 405 to the electromagnet 801 and the electromagnet 802, an inner diameter of the flow path 402, a flow rate of an electrolytic solution flowing through the flow path 402, and a ON/OFF time of the current flowing through the electromagnet 801 and the electromagnet 802.

EXAMPLE 3

Next, an analysis device of Example 3 of the invention will be described with reference to FIG. 9. FIG. 9 is a view explaining a second step according to one embodiment of the analysis device disclosed in Example 3 of the invention. The configuration of the analysis device of this example which is different from that in Example 1 will be described. This example is different therefrom in that the particle distribution measurement device used for the measurement of the amount of the complex is respectively provided in the flow path for mass spectrometry 406 and flow path for immunological analysis 407 in the separation unit 210 in the second step 102. In this example, only the second step 102 is different from that in Example 1 and other configurations are the same. The configuration of the analysis device of this example will be described.

The separation unit 210 of this example is configured with the injector 401 which introduces the complex discharged from the reaction solution probe 209 to the separation unit 210, the flow path 402, the pump 403 which is positioned in a front stage of the injector 401 and sends a solvent to the flow path 402, the active flow splitter 404 which is positioned at a branched portion of the flow path 402, the flow path for mass spectrometry 406 which is positioned in the rear stage of the active flow splitter 404 and sends the complex to the mass spectrometry unit 211, the flow path for immunological analysis 407 which is positioned in the rear stage of the active flow splitter 404 and sends the complex to the immunological analysis unit 212, a particle distribution measurement device 901 which is provided on the flow path for mass spectrometry 406, and a particle distribution measurement device 902 which is provided on the flow path for immunological analysis 407.

The separation unit 210 has a mechanism of measuring the amount of the complex using the particle distribution measurement device 901 and the particle distribution measurement device 902 provided on the flow path for mass spectrometry 406 and the flow path for immunological analysis 407, and calculating amount of the complex introduced to the mass spectrometry unit 211 and the immunological analysis unit 212.

EXAMPLE 4

Next, an analysis device of Example 4 of the invention will be described with reference to FIG. 10. FIG. 10 is a schematic view showing a schematic configuration according to one embodiment of the analysis device disclosed in Example 4 of the invention. The configuration of the analysis device of this example which is different from that in Example 1 will be described. This example is different therefrom in that the separation is performed by sucking and discharging the complex from the reaction container 206 to a separation container 1002 using a dedicated separation probe 1003 in an off-line state in the separation unit 210 in the second step 102. In this example, only the second step 102 is different from that in Example 1 and other steps are the same. The configuration of the analysis device of this example will be described.

The separation unit 210 of this example is configured with the separation container 1002 which receives the complex discharged from the reaction solution probe 209, a separation container transportation unit 1001 which transports the separation container 1002, and a separation probe 1003 which sucks a given amount of the complex from the separation container 1002 and introduces the complex to the mass spectrometry unit 211 and the immunological analysis unit 212.

A flow of the measurement of this example will be described. The reaction container transportation unit 205 and the separation container transportation unit 1001 rotate to a predetermined position below the reaction solution probe 209. The total amount of the complex suspended in a slurry form is sucked and discharged from the reaction container 206 to the separation container 1002 by using the reaction solution probe 209. Next, the separation container transportation unit 1001 rotates to a predetermined position below the separation probe 1003, and a given amount of the complex is introduced from the separation container 1002 to the mass spectrometry unit 211 and the immunological analysis unit 212 by using the separation probe 1003. The separation probe 1003 can suck and discharge a given amount of the complex, and accordingly, it is possible to calculate the amount of the complex introduced to the mass spectrometry unit 211 and the immunological analysis unit 212.

EXAMPLE 5

Next, an analysis device of Example 5 of the invention will be described. This example is different therefrom in that a plurality of substances being measured can be simultaneously measured using the magnetic beads to which plural kinds of antibodies are bonded. In this example, the magnetic beads to which anti-triiodothyronine antibody (anti-FT3 antibody) is bonded and the magnetic beads to which anti-thyroxine antibody (anti-FT4 antibody) is bonded, are mixed with each other and measurement is performed. In this example, a point of using the magnetic beads to which plural kinds of antibodies are bonded is different from that in Example 1 and other steps are the same. First, a complex in which the magnetic beads previously bonded with an antibody, and triiodothyronine, thyroxine, and similar compounds are bonded to each other is formed. The complex is separated to the mass spectrometry unit 211 and the immunological analysis unit 212 by the separation unit 210 to perform the measurement regarding the complex. Accordingly, the total amount of triiodothyronine, thyroxine, and similar compounds is quantified in the mass spectrometry unit 211 and proportions of peak intensity of triiodothyronine, thyroxine, and similar compounds are measured in the immunological analysis unit 212. The quantification of triiodothyronine and thyroxine is performed from the total amount and the proportions of peak intensity of triiodothyronine, thyroxine, and similar compounds. In this example, accurate quantitative values of triiodothyronine and thyroxine which have reduced cross reactivity of antibodies can be calculated, and thus, panel inspection of biomarker of a disease of the thyroid gland with excellent precision can be performed. In the related art, triiodothyronine and thyroxine have been respectively measured by using the immunological analysis method, but with this example, the measurement can be simultaneously performed and the throughput is improved.

REFERENCE SIGNS LIST

101: first step
102: second step
103: third step
104: fourth step
105: fifth step
201: sample transportation unit
202: sample container
203: reagent transportation unit
204: reagent container
205: reaction solution transportation unit
206: reaction container
207: sample probe
208: reagent probe
209: reaction solution probe
210: separation unit
211: mass spectrometry unit
212: immunological analysis unit
213: control unit
214: magnet
301: magnetic beads
302: avidin
303: biotin
304: antivitamin D antibody
305: substance being measured
306: similar compound
401: injector
402: flow path
403: pump
404: active flow splitter
405: particle distribution measurement device
406: flow path for mass spectrometry
407: flow path for immunological analysis
501: magnet
502: reagent container for immunological analysis
503: reagent transportation unit for immunological analysis
504: probe for immunological analysis
505: light source
506: photometer
601: flow path
602: magnet
603: ion source
604: mass spectrometer
801: electromagnet (flow path for immunological analysis)
802: electromagnet (flow path for mass spectrometry)
1001: separation container transportation unit
1002: separation container
1003: separation probe

The invention claimed is:

1. An analysis device comprising:
a sample transport which transports a sample container;
a reagent transport which transports a reagent container;
a reaction solution transport which transports a reaction container in which reactions are carried out;

a sample probe which sucks and discharges a sample from the sample container to the reaction container;

a reagent probe which sucks and discharges reagents from the reagent container to the reaction container;

a reaction solution probe which sucks and discharges a complex reacted in the reaction container to a separator;

the separator which quantitatively separates the complex into a first amount for immunological analysis and into a second amount for mass spectrometry;

a mass spectrometer which performs measurement of the second amount of the complex;

an immunological analyzer which performs measurement of the first amount of the complex using a light source and photometer; and a processor which performs data processing.

2. The analysis device according to claim 1,
wherein the separator includes a flow path including a branched portion which branches into a first flow path and a second flow path, an injector which introduces the complex discharged from the reaction solution probe to the flow path upstream of the branched portion, a pump for sending a solvent to the flow path and positioned upstream of the injector, an active flow splitter positioned on the branched portion of the flow path, a counter which measures an amount of the complex in the flow path between the injector and the active flow splitter in real time, the second flow path for mass spectrometry is positioned downstream of the active flow splitter and sends the second amount of the complex to the mass spectrometer, and the first flow path for immunological analysis is positioned downstream of the active flow splitter and sends the first amount of the complex to the immunological analyzer.

3. The analysis device according to claim 1,
wherein the separator includes a flow path including a branched portion which branches into a first flow path and a second flow path, an injector which introduces the complex discharged from the reaction solution probe to the flow path upstream of the branched portion, a pump for sending a solvent to the flow path and positioned upstream of the injector, a counter which is provided in the flow path between the branched portion and the injector, the second flow path for mass spectrometry sends the second amount of the complex to the mass spectrometer, the first flow path for immunological analysis sends the first amount of the complex to the immunological analyzer, a first magnet positioned adjacent the second flow path for mass spectrometry, and a second magnet positioned adjacent the first flow path for immunological analysis.

4. The analysis device according to claim 1,
wherein the separator includes a flow path including a branched portion which branches into a first flow path and a second flow path, an injector which introduces the complex discharged from the reaction solution probe to the flow path upstream of the branched portion, a pump for sending a solvent to the flow path and positioned upstream of the injector, an active flow splitter positioned at the branched portion of the flow path, the second flow path for mass spectrometry is positioned downstream of the active flow splitter and sends the second amount of the complex to the mass spectrometer, the first flow path for immunological analysis is positioned downstream of the active flow splitter and sends the first amount of the complex to the immunological analyzer, a first counter which is provided on the second flow path for mass spectrometry, and a second counter which is provided on the first flow path for immunological analysis.

5. The analysis device according to claim 1,
wherein the separator includes a separation container which receives the complex discharged from the reaction solution probe, a separation container transport which transports the separation container, and a separation probe which sucks a given amount of the complex from the separation container and introduces the complex to the mass spectrometer and the immunological analyzer.

6. The analysis device according to claim 1,
wherein the processor performs quantification of substances being measured from data acquired by the mass spectrometer and data acquired by the immunological analyzer.

7. The analysis device according to claim 6,
wherein the data acquired by the mass spectrometer is the total amount of the substances being measured and similar compounds configuring the complex, and the data acquired by the immunological analyzer is proportions of the substances being measured and similar compounds configuring the complex.

* * * * *